Figure 1:
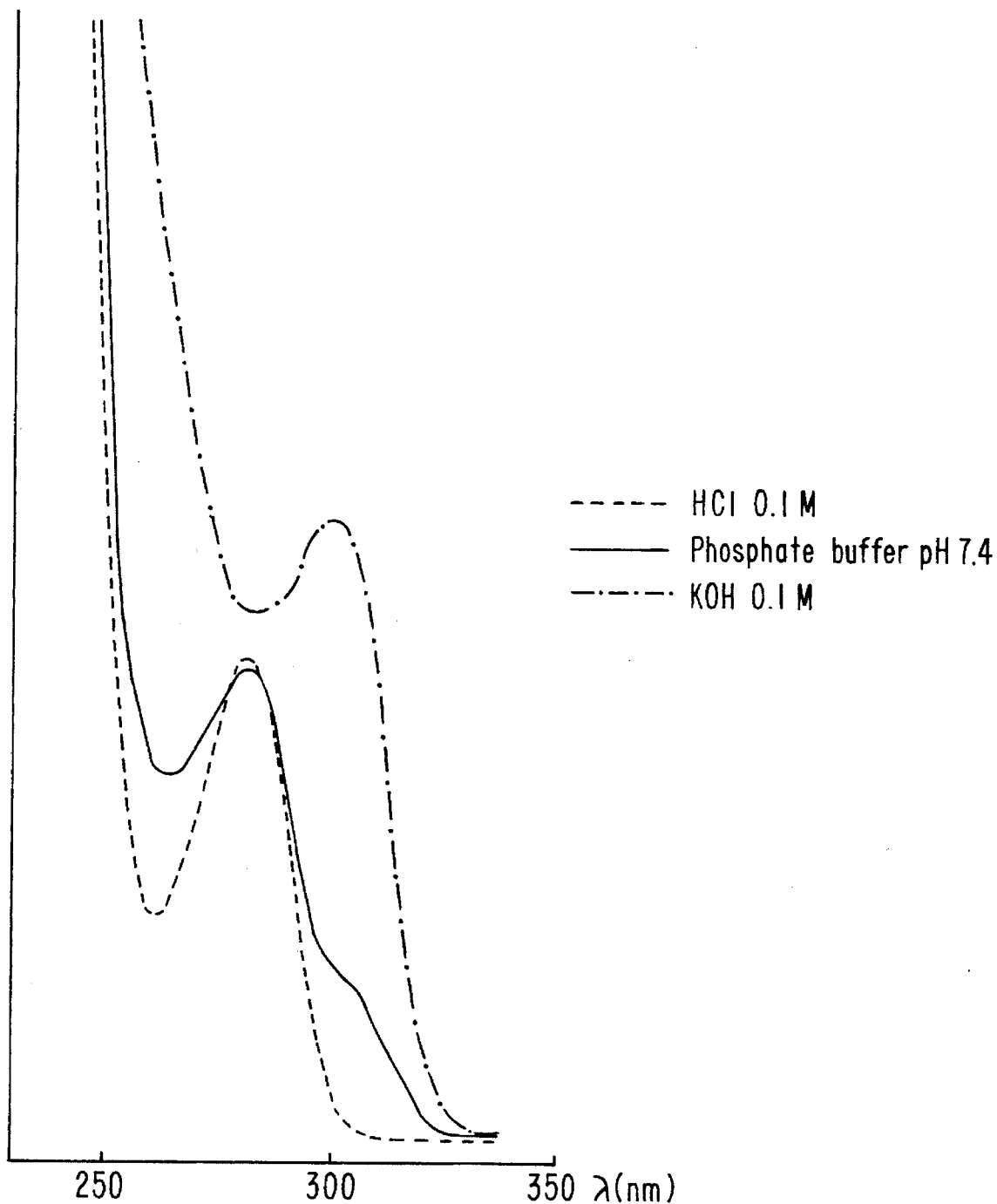

United States Patent [19]

Selva et al.

[11] Patent Number: 5,567,676

[45] Date of Patent: Oct. 22, 1996

[54] GLYCOPEPTIDE ANTIBIOTICS

[75] Inventors: Enrico Selva, Gropello Cairoli; Grazia Beretta, Milan; Angelo Borghi, Milan; Maurizio Denaro, Milan, all of Italy

[73] Assignee: Gruppo Lepetit S.p.A, Gerenzano, Italy

[21] Appl. No.: 457,365

[22] Filed: Jun. 1, 1995

Related U.S. Application Data

[63] Continuation of Ser. No. 317,430, Oct. 4, 1994, abandoned, which is a continuation of Ser. No. 347,980, filed as PCT/EP87/00588, Oct. 8, 1987, abandoned.

[30] Foreign Application Priority Data

Oct. 10, 1986 [GB] United Kingdom .................. 8624400
Nov. 4, 1986 [GB] United Kingdom .................. 8626324

[51] Int. Cl.$^6$ ........................ A61K 38/14; A61K 38/12; C07K 9/00
[52] U.S. Cl. .................. 514/8; 424/115; 424/116; 424/117; 424/118; 424/119; 424/120; 424/121; 424/122; 424/123; 514/11; 530/317
[58] Field of Search ................... 424/115, 116, 424/117, 118, 119, 120, 121, 122, 123; 530/317; 514/8, 9, 11

[56] References Cited

U.S. PATENT DOCUMENTS

| | | | |
|---|---|---|---|
| 3,780,174 | 12/1973 | Hamill et al. | 424/118 |
| 4,115,552 | 9/1978 | Hamill et al. | 424/118 |
| 4,239,751 | 12/1980 | Coronelli et al. | 424/118 |
| 4,375,513 | 3/1983 | Debono et al. | 435/169 |
| 4,782,042 | 11/1988 | Selva et al. | 530/317 |

FOREIGN PATENT DOCUMENTS

| | | |
|---|---|---|
| 20055071 | 6/1982 | European Pat. Off. . |
| 30177882 | 4/1986 | European Pat. Off. . |

OTHER PUBLICATIONS

Gilman, A. G., Rall, T. W., Nies, A. S., Taylor, P., Ed., *Goodman and Gilman's The Pharmacological Basis of Therapeutics* 8th ed., Pergamon Press, (1990), pp. 1018–1034.
Demain, A. L., Solomon, N. A., Ed., *Manual of Industrial Microbiology and Biotechnology*, American Soc. for Microbiology, (1986), pp. 24–26.
Gennaro, A. R., *Remington's Pharmaceutical Sciences* 18th ed., Pharmaceutical Sciences, (1990), pp. 757, 1163, 1214–1215.
Williams, S. T., Ed., *Bergey's Manual of Systematic Bacteriology* vol. 4., Williams & Wilkins, (1989), pp. 2418–2428.
R. Gherna, P. Pienta, R. Cote, Ed., *ATCC Catalogue of Bacteria & Bacteriophages* 17th ed., (1989), p. 10.
R. Gherna, P. Pienta, R. Cote, Ed., *ATCC Catalogue of Bacteria & Bacteriophages* 18th ed., (1992), p. 16.
Kirk–Othmer, Encyclopedia of Chemical Technology, 3rd Edition, vol. 2, A Wileyz–Interscience publication p. 809 (1978).
S. K. Chung, *The Journal of Antibiotics* 39: pp. 652–659, (1986).

*Primary Examiner*—Howard E. Schain
*Attorney, Agent, or Firm*—Ruth E. Homan

[57] ABSTRACT

The present invention concerns new antiobiotic substances demoninated de-acyl antibiotics A40926, de-acyl antibiotic A 40926P and antibiotic A 40926 amino glucronyl aglycon, and the use of these substances in the treatment of infectious diseases involving microorganisms susceptible to it.

10 Claims, 3 Drawing Sheets

GLYCOPEPTIDE ANTIBIOTICS

This is a continuation of Ser. No. 08/317,430, filed Oct. 4, 1994, now abandoned, which is a continuation of Ser. No. 07/347,980, filed as PCT/EP87/00588 on Oct. 8, 1987, which is now abandoned.

Antibiotic A 40926 is a glycopeptidic antibiotic which has been isolated from a culture of Actinomadura, named Actinomadura sp. ATCC 39727. It is a complex whose factors have been named factor A, factor B, factor $B_0$, factor PA and factor PB. It was described in EP-A-177882.

Antibiotic A 40926 can be transformed into the corresponding N-acylaminoglucuronyl aglycon derivatives by acid hydrolysis under controlled conditions as described in EP 86117452.

Antibiotic A 40926 complex, the factors thereof, the corresponding N-acylaminoglucuronyl aglycon complex and factors thereof, are active mainly against gram positive bacteria and Neisseriae.

The present invention is directed to new de-acyl derivatives of the above named compounds, which share the common feature of having an N-acylaminoglucuronyl group linked to a peptidic moiety through an O-glycosidic bond. They are named de-acyl antibiotic A 40926, de-acyl antibiotic A 40926 P and antibiotic A 40926 aminoglucuronyl aglycon and can be represented by the following formula I (the numbering is analogous to that suggested by Williams J. et al. in J. Am. Chem. Soc., 106, 4895–4908 (1984) for other glycopeptidic antibiotics):

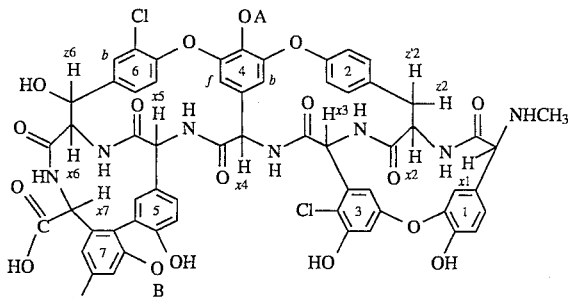

wherein:

A represents a 2-amino-2-deoxy-beta-D-glucopyranosiduronic acid group and

B represents hydrogen, alpha-D-mannopyranosyl or 6-acetyl-alpha-D-mannopyranosyl, and the addition salts thereof.

These de-acylated derivatives will be collectively referred to as "de-acyl A 40926 antibiotics" and generically each of them will be referred to as a "de-acyl A 40926 antibiotic".

The above named starting materials, i.e. antibiotic A 40926 complex and factors thereof, the corresponding N-acylaminoglucuronyl aglycon complex and factors thereof, can be represented by the above formula I wherein A represents a 2-deoxy-2-($C_{11}$–$C_{12}$)acylaminobeta-D-glucuronyl group and B represents hydrogen, an alpha-D-mannosyl or 6-acetyl-alpha-D-mannosyl group, or an addition salt thereof.

More particularly, antibiotic A 40926 factor A is the compound of the above formula wherein A represents 2-deoxy-2-undecanoylamino-beta-D-glucopyranosiduronyl and B represents mannosyl, antibiotic A 40926 factor $B_0$ is the compound of the above formula wherein A represents 2-deoxy-2- isododecanoylamino-beta-D-glucuronyl and B represents alpha-D-mannosyl, antibiotic A 40926 factor $B_1$ is the compound of the above formula wherein A represents 2-deoxy-2-dedecanoylamino-beta-D-glucuronyl and B represents alpha-D-mannosyl.

Antibiotic A 40926 factors of the "P" series, such as factor PA and factor $PB_0$, differ from the corresponding factors (factor A and $B_0$ respectively), in that the mannose unit is replaced by a 6-acetyl-mannose unit.

Antibiotic A 40926 N-acylaminoglucuronyl aglycons are represented by the above formula wherein A is as defined above and B represents hydrogen. Their acyl chain on the aminoglucuronyl group corresponds to those of the single factors of antibiotic A 40926.

On the basis of the data available and by reference to known substances, one may attribute to de-acyl antibiotic A 40926 the above formula wherein the A represents 2-amino-2-deoxy-beta-D-glucuronyl and B represents alpha-D-mannosyl, to de-acyl antibiotic A 40926 P the above formula wherein A represents 2-amino-2-deoxy-beta-D-glucuronyl and B represents 6-acetyl-alpha-D-mannosyl and to antibiotic A 40926 aminoglucuronyl aglycon the above formula wherein A represents 2-amino-2-deoxy-beta-D-glucuronyl and B represents hydrogen.

Antibiotic A 40926 factors PA and PB, at least under certain fermentation conditions, are the main antibiotic products of the A 40926 producing microorganism.

Antibiotic A 40926 factors A and B are mainly transformation products of antibiotic A 40926 factor PA and factor PB, respectively, and are often-already present in the fermentation broth.

It has been found that antibiotic A 40926 factor PA can be transformed into antibiotic A 40926 factor A and antibiotic A 40926. factor PB can be transformed into antibiotic A 40926 factor B under basic conditions which lead to the removal of the acetyl group of the mannose unit without displacing the acyl group on the aminoglucuronyl unit.

As a consequence, when the fermentation broth, or an antibiotic A 40926 containing extract or concentrate thereof, is allowed to stand for a certain time under basic conditions (e.g. aqueous solution of a nucleophilic base, at a pH>9 overnight,) an antibiotic A 40926 complex will be obtained which is enriched in antibiotic A 40926 factor A and factor B (see EP-A-177882).

The same type of basic transformation can be applied to the conversion of de-acyl antibiotic A 40926 P to de-acyl antibiotic A 40926.

De-acyl antibiotic A 40926 has the following physicochemical characteristics:

A) ultraviolet absorption spectrum, which is shown in FIG. 1 of the accompanying drawings, and exhibits the following absorption maxima:

|  | λ max (nm) |
|---|---|
| a) 0.1M HCl | 282 |
| b) phosphate buffer pH 6.0 | 281 |
| c) phosphate buffer pH 7.4 | 282, 300 (shoulder) |
| d) 0.1M KOH | 300 |

Figure 2:
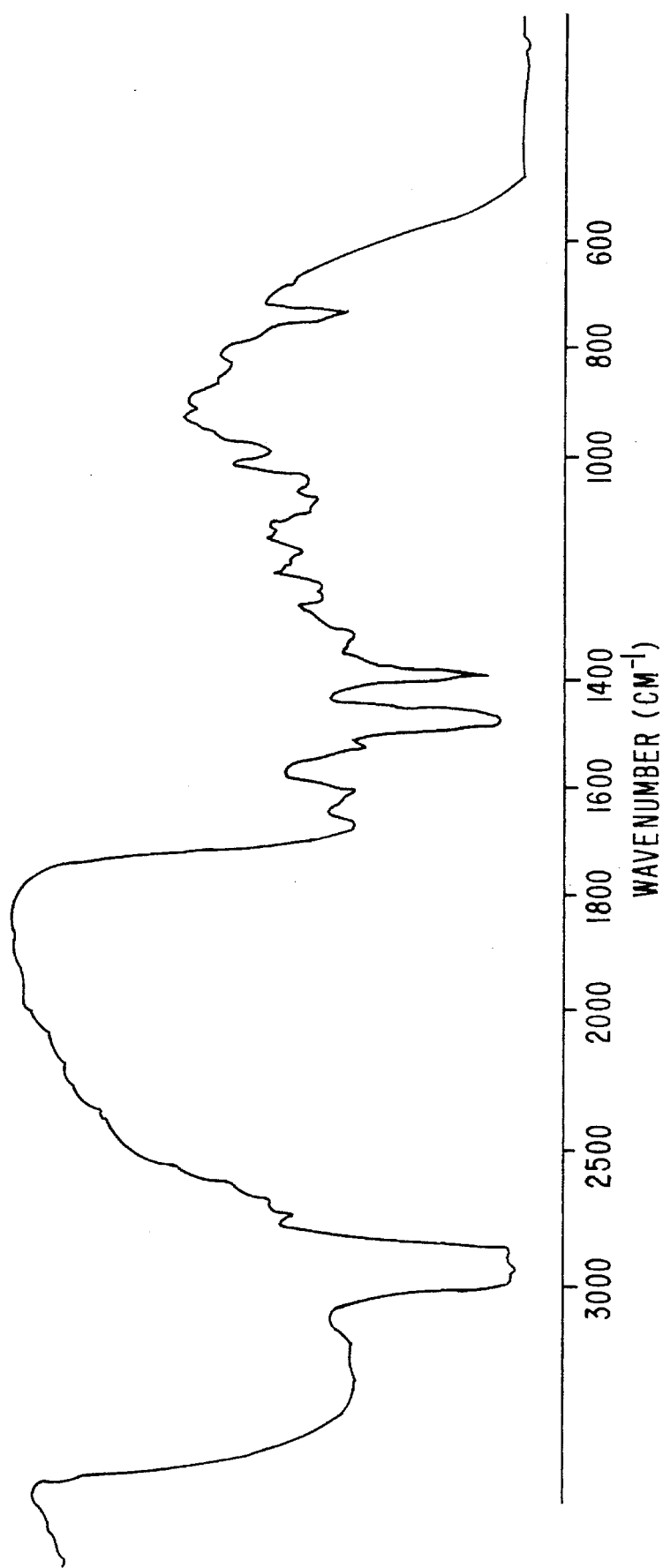

B) infrared absorption spectrum which is shown in FIG. 2 of the accompanying drawings and exhibits the following absorption maxima in nujol mull (v, $cm^{-1}$): 3700–3100; 3000–2800 (nujol); 1650; 1590; 1505; 1460 (nujol); 1375 (nujol); 1300; 1230, 1210, 1150, 1060, 1030, 970, 810, 720 (nujol)

Figure 3:
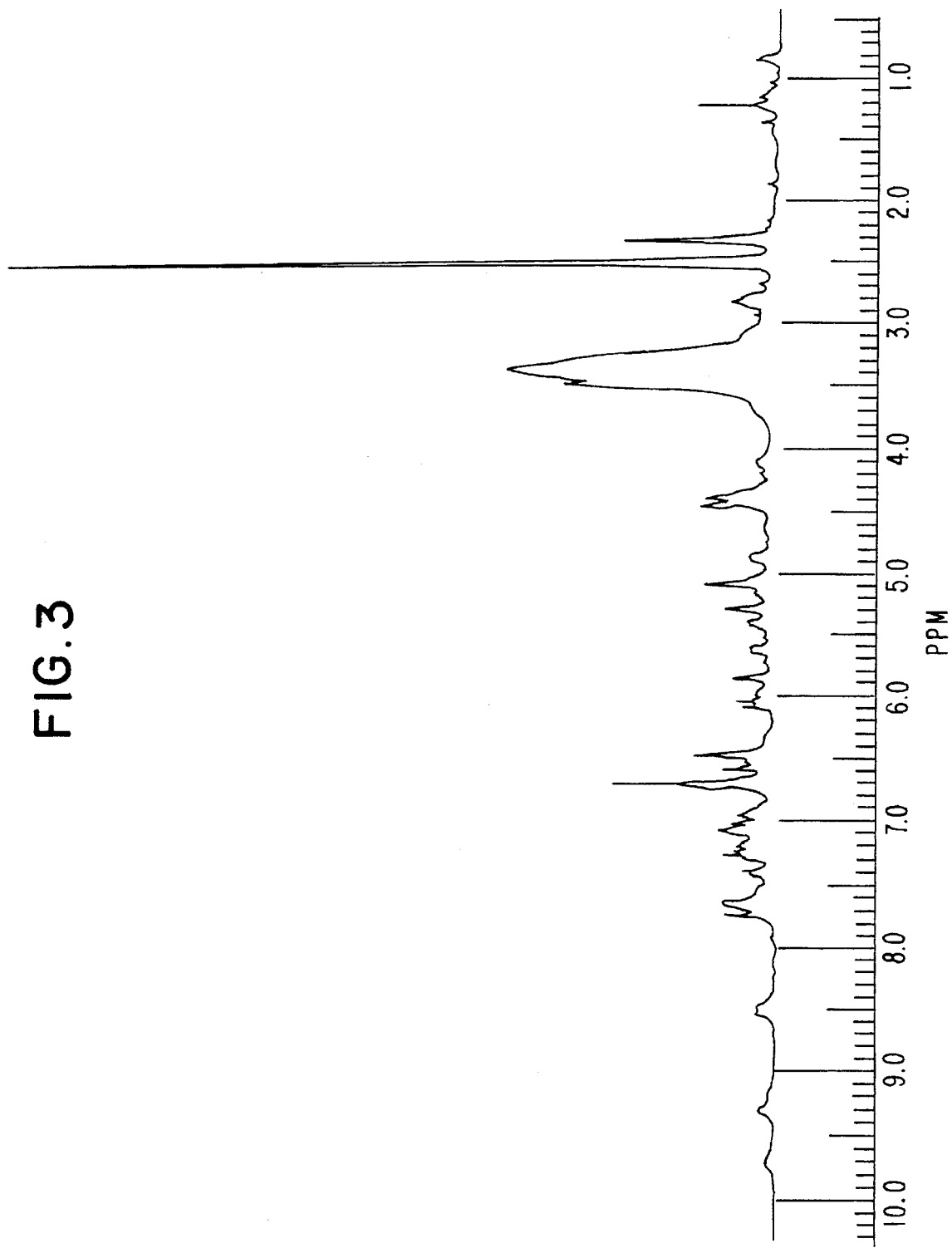

C) $^1$H-NMR spectrum which is shown in FIG. 3 of the accompanying drawings and exhibits the following groups of signals (in ppm) at 270 MHz recorded in DMSO $d_6$ (hexadeuterodimethylsulfoxide) [(δ, ppm; m; (attributions)]

2.30, s (N—$CH_3$); 2.49, s (DMSO$d_5$); 2.7–3.8, m (sugar CH's); 2.79 m (Z2); 4.08 m (X6); 4.33 s (X1); 4.37 d (X5);

4.37 d (X7); 4.86 m (X2); 5.08 s (4f); 5.08 s (Z6); 5.27 s (anomeric proton of mannose); 5.35 d (anomeric proton of aminoglucuronic acid); 5.61 d (X4); 5.86 s (4b); 6.05, d (X3); 7.73 s (6b); 6.45–8.49 (aromatic protons and peptidic NH's) s=singlet; d=doublet; m=multiplet D) Retention time ($R_t$) of 0.34 relative to Vancomycin (Eli Lilly) Column: Silanized silica gel ULTRASPHERE ODS (5 μm) 4.6 mm×25 cm ALTEX (Beckman) Isocratic elution with 18 mM sodium phosphate buffer/$CH_3CN$ 92/8 (v/v) Flow rate: 1.8 ml/min Detection: UV 254 nm Internal standard: Vancomycin (Eli Lilly) $R_t$ 8.4 min E) Molecular weight of 1548 as determined by FAB-MS spectroscopy.

By comparison with the physico-chemical data of the starting materials with reference in particular to the NMR spectrum, one may note that the peaks corresponding to aliphatic protons in the range 0.8–2.0 ppm are no longer present in the new molecule.

Isosensitest broth (Oxoid), 24 h, for staphylococci, *Strep. faecalis* and Gram-negative bacteria (*Escherichia coli, Klebsiella pneumoniae*); Todd-Hewitt broth (Difco), 24 h for other streptococcal species; GC base broth (Difco) +1% Isovitalex (BBL), 48 h, $CO_2$-enriched atmosphere for *Neisseria gonorrhoeae*; Brain Heart broth (Difco) +1% Supplement C (Difco), 48 h for *Haemophilus influenzae*; AC broth (Difco), 24 h, anaerobic atmosphere for *Clostridium perfringens*; PPLO broth with supplements as in R. T. Evans and D. Taylor-Robinson (J. Antimicrob. Cheroother. 4, 57), 24 h for *U. urealyticum*. Incubation was at 37° C. Inocula were as follows: about $10^4$ color-changing units/ml for *U. urealyticum*; about $10^4$–$10^5$ colony-forming units/ml for other broth dilution MICs.

The minimal inhibitory concentrations (MIC, microg/ml) for some microorganisms are reported below in Table I.

TABLE I

| Strain | M.I.C. (microg/ml) De-acyl Antibiotic A 40926 |
| --- | --- |
| Staph. aureus L165 | 1 |
| Staph. aureus ($10^6$ cfu/ml) | 2 |
| Staph. aureus (30% bovine serum) | 2 |
| Staph. epidermidis L147 ATCC 12228 (coagulase negative) | 2 |
| Staph. haemolyticus L602 (clinical isolate) | 32 |
| Strep. pyogenes L49 C203 | 0.25 |
| Strep. pneumoniae L44 UC41 | 0.25 |
| Strep. faecalis L149 ATCC 7080 | 2 |
| Strep. mitis L796 (clinical isolate) | 0.5 |
| Clostridium perfringens L290 ISS 30543 | 0.13 |
| Neisseria gonorrhoeae L997 ISM68/126 | 64 |
| Haemophilus influenzae L 970 type b ATCC 19418 | 128 |
| Escherichia coli L47 SKF 12140 | >128 |
| Proteus vulgaris L79 X19H ATCC881 | >128 |
| Pseudomonas aeruginosa L4 ATCC10145 | >128 |
| Ureaplasma urealyticum L1479 (clinical isolate) | >128 |
| Klebsiella pneumoniae L142 | >128 |

Also in the case of de-acyl antibiotic A 40926 P and antibiotic A 40926 aminoglucuronyl aglycon, the main difference between the NMR spectra of these compounds and the corresponding "acylated" ones is the absence of signals of aliphatic protons in the range 0.8–2.0 ppm.

More particularly, the $^1$H-NMR spectrum of deacyl antibiotic A 40926 P have the following groups of signals (ppm) at 270 MHz, recorded in DMSO $d_6$ [δppm, m, (attribution)]:

2.0, s ($CH_3CO$); 2.3, s ($NCH_3$); 2.5, s (DMSO $d_5$); 2.7–3.8, m (sugar CH's); 2.8, m (Z2); 4.1, m ($X_6$); 4.1, m ($CH_2O$, sugar); 4.4 s (X1); 4.4 d (X5); 4.4 d (X7); 4.9 m (X2); 5.1, s (4f); 5.1, s, (Z6); 5.3, s (anomeric proton mannose); 5.4, d (anomeric proton aminoglucuronic acid); 5.6, d (X4); 5.8, s (4b); 6.1 d (X3); 7.7, s (6b); 6.5–8.6 (aromatic and peptidic NH's).

The $^1$H-NMR spectrum of antibiotic A 40926 aminoglucuronyl aglycon have the following group of signals (ppm) at 270MHz, recorded in DMSO $d_6$ [δppm, m, (attribution)]:

2.3, s ($NCH_3$); 2.5, s (DMSO $d_5$); 2.7–3.8 m (sugar CH's); 2.8, m (Z2); 4.1, m (X6); 4.4, s (X1); 4.4, d (X5); 4.4 d (X7); 4.9, m (X2); 5.1, s (4f); 5.1, s (Z6); 5.4 d (anomeric proton aminoglucuronic acid); 5.5 d (X4); 5.7, s (4b); 6.1, d (X3); 7.7, s (6b); 6.2–8.5 (aromatic and peptidic NH's).

The antibacterial activity of the compounds of the invention can be demonstrated in vitro by means of standard dilution tests on different microorganism cultures.

Culture media and growth conditions for MIC (minimal inhibitory concentration) determinations were as follows:

Antibiotic A 40926 aminoglucuronyl aglycon and de-acyl antibiotic A 40926 P show substantially the same level of antimicrobial activity as that reported above for de-acyl antibiotic A 40926.

The antimicrobial activity of the compounds of the invention is confirmed also in experimental septicemia in the mice.

Control and treatment groups may include ten CD-1 mice (Charles River) weighing 18–22 g. They are infected intraperitoneally with 0.5 ml of bacterial suspension prepared by diluting an overnight culture of *S. pyogenes* C 203 (L 49) with sterile peptonized saline. Inocula are adjusted so that untreated animals die of septicemia within 48 h. The compounds to be tested are administered subcutaneously immediately after infection. On the 7th day, the $ED_{50}$ in mg/kg is calculated by the method of Spearman and Kärber (D. J. Finney "Statistical Methods in Biological Assay" Griffin, page 524, 1952) from the percentage of surviving animals at each dose.

For example, under these conditions the $ED_{50}$ of de-acyl antibiotic A 40926 is 2.33 mg/kg, s.c.

The de-acyl A 40926 antibiotics possess acid and basic functions and can form salts with organic and inorganic counter ions according to conventional procedures.

Representative and suitable acid addition salts of the compounds of the invention include those salts formed by standard reaction with both organic and inorganic acids such as, for example, hydrochloric, hydrobromic, sulfuric, phosphoric, acetic, trifluoroacetic, trichloroacetic, succinic, citric, ascorbic, lactic, maleic, fumaric, palmitic, cholic, pamoic, mucic, glutamic, camphoric, glutaric, glycolic, phthalic, tartaric, lauric, stearic, salicylic, methanesulfonic, benzenesulfonic, sorbic, picric, benzoic, cinnamic and the like acids.

Representative examples of these bases are: alkali metal or alkaline-earth metal hydroxide such sodium, potassium, calcium, magnesium, barium hydroxide; ammonia and aliphatic, alicyclic or aromatic organic amines such as methylamine, dimethylamine, trimethylamine, and picoline.

The transformation of the "non-salt" compounds of the invention into the corresponding addition salts, and the reverse, i.e. the transformation of an addition salt of a compound of the invention into the non-salt form, are within the ordinary technical skill and are encompassed by the present invention.

For instance de-acyl antibiotic A 40926, antibiotic A 40926 aminoglucuronyl aglycon or de-acyl antibiotic A 40926 P can be transformed into the corresponding acid or base addition-salt by dissolving the non-salt form in an aqueous solvent and adding a slight molar excess of the selected acid or base. The resulting solution or suspension is then lyophilized to recover the desired salt.

In case the final salt is insoluble in a solvent where the non-salt form is soluble it is recovered by filtration from the organic solution of the non-salt form after addition of the stoichiometric amount or a slight molar excess of the selected acid or base.

The non-salt form can be prepared from a corresponding acid or base salt dissolved in an aqueous solvent which is then neutralized to free the non-salt form.

When following this step, the elimination of an excess of acid or base is necessary, a common desalting procedure may be employed.

For example, column chromatography on silanized silica gel, non-functionalized polystyrene, acrylic and controlled pore polydextrane resins (such as SEPHADEX LH 20) or activated carbon may be conveniently used. After eluting the undesired salts with an aqueous solution, the desired product is eluted by means of a linear gradient or a step-gradient of a mixture of water and a polar or apolar organic solvent, such as acetonitrile/water from 50:50 to about 100% acetonitrile.

As it is known in the art, the salt formation either with pharmaceutically acceptable acids (or bases) or non-pharmaceutically acceptable acids (or bases) may be used as a convenient purification technique. After formation and isolation, the salt form of an A 40926 antibiotic can be transformed into the corresponding non-salt form or into a pharmaceutically acceptable salt form.

In some instances, a base addition salt of a de-acyl A 40926 antibiotic is more soluble in water and hydrophilic solvents.

The de-acyl antibiotic A 40926, de-acyl antibiotic A 40926 P and antibiotic A 40926 aminoglucuronyl aglycon are prepared from antibiotic A 40926 complex or a factor thereof, antibiotic A 40926 factor PA or factor PB or a mixture thereof, and antibiotic A 40926 N-acylaminoglucuronyl aglycon complex or a factor thereof, respectively, by a microbiological transformation with suitable Actinoplanes strains such as *Actinoplanes teichomyceticus* ATCC 31121, *Actinoplanes missouriensis* ATCC 23342, *Actinoplanes missouriensis* NRRL 15647 or NRRL 15646, and Actinoplanes NRRL 3884. *Actinoplanes teichomyceticus* ATCC 31121 is described in U.S. Pat. No. 4,239,751, *Actinoplanes missouriensis* ATCC 23342 is described in U.S. Pat. No. 3,952,095, *Actinoplanes missouriensis* NRRL 15647 and NRRL 15646 are described in U.S. Pat. No. 4,587,218, while Actinoplanes NRRL 3884 is described in U.S. Pat. No. 3,780,174. All these strains are available from the respective culture collections.

More particularly, the selected starting material, either in pure form or in the form of any crude preparations thereof, including harvested fermentation broth of Actinomadura sp. ATCC 39727 or a producing mutant or variant thereof, is contacted with a culture of an Actinoplanes strain such as *Actinoplanes teichomyceticus* ATCC 31121, *Actinoplanes missouriensis* ATCC 23342, *Actinoplanes missouriensis* NRRL 15646, *Actinoplanes missouriensis* NRRL 15647 or Actinoplanes NRRL 3884, preferably during fermentation.

An Actinoplanes strain, such as preferably, Actinoplanes teichomyceticusATCC 31121, *Actinoplanes missouriensis* ATCC 23342, *Actinoplanes missouriensis* NRRL 15646, *Actinoplanes missouriensis* NRRL 15647 or Actinoplanes NRRL 3884, are cultivated under usual submerged aerobic conditions in a medium containing assimilable sources of carbon, nitrogen and inorganic salts. Examples of such media are those reported in the above cited U.S. patents and those generally known in the art.

Generally, the starting material mentioned above can be added to a culture of an Actinoplanes strain such as preferably *Actinoplanes teichomyceticus* ATCC 31121, *Actinoplanes missouriensis* ATCC 23342, *Actinoplanes missouriensis* NRRL 15646, *Actinoplanes missouriensis* NRRL 15647 or Actinoplanes NRRL 3884, at a time varying from time zero to the time at which the culture has reached its maximum growth. Addition after 36–72 h of growth is, at least in some instances, preferred.

The reaction temperature is generally between 20° C. and 40° and preferably between 24° C. and 35° C. and most preferably between 25° C. and 32° C.

The reaction time, i.e. the time of exposure of the starting material to the microbial culture environment before recovering the final product, may vary between 100 and 300 h, depending on the specific conditions employed. Anyway, since the reaction can be monitored as known in the art, for instance by following the decrease of the starting material and/or the increase of the final product by-HPLC, the-skilled man is capable of readily determine when the reaction is to be considered as complete and the recovery procedure can be started.

Instead of employing a growing culture of an Actinoplanes strain such as *Actinoplanes teichomyceticus* ATCC 31121, *Actinoplanes missouriensis* ATCC 23342, *Actinoplanes missouriensis* NRRL 15646, *Actinoplanes missouriensis* NRRL 15647 or Actinoplanes NRRL 3884, one may employ a culture of any mutant or variant thereof which is still capable of de-acylating the above mentioned starting material to give the de-acylated compounds of the invention. Any process according to the present invention which employs any such mutant or variant, is considered to be encompassed by the scope of the present invention, Actually, *Actinoplanes missouriensis* NRRL 15646 and NRRL 15647 are obtained by chemical mutagensis of *Actinoplanes missouriensis* ATCC 31683 which is in turn a mutation product of *Actinoplanes missouriensis* ATCC 23342. *Actinoplanes missouriensis* ATCC 31683 is described in U.S. Pat. Nos. 4,322,406 and 4,375,513 with *Actinoplanes missouriensis* ATCC 31682 and ATCC 32680 and is available from the culture collection as the other mentioned Actinoplanes strains.

A mutant strain of *Actinoplanes teichomyceticus* ATCC 31121 was deposited on July 21, 1987 with ATCC where it received accession number 53649. This strain was deposited under the provisions of the Budapest Treaty.

Instead of using single pure cultures of the above deacylating microorganisms, one may use a mixture thereof in any proportion.

The compounds of the present invention can be prepared according to the method of the invention also by using the washed mycelium of one of the above identified de-acylating microorganism cultures, conveniently re-suspended in a physiologically acceptable medium, a cell-free preparation obtained by disrupting the cells, e.g. by sonication and collecting the debris by centrifugation, or a cell-free water soluble extract or concentrate obtained from a disrupted cell preparation. Reaction time and temperature may require a certain adaptation in this case, but substantially mirror those indicated above for the whole microbial culture, even if the temperature may be increased, at least in some instances, up to 50°–60° C., and preferably is between 25° C. and 50° C.

The recovery of the antibiotic substances from the reaction medium is then conducted according to known per se techniques which include extraction with solvents, precipitation by adding non-solvents or by changing the pH of the solution, partition chromatography, reverse-phase partition chromatography, ion-exchange chromatography, affinity chromatography and the like.

A preferred procedure includes an affinity chromatography on immobilized D-Alanyl-D-Alanine followed by separation at a different pH.

Immobilized D-Alanyl-D-Alanine matrices suitable for the present recovery process are disclosed in European Patent Application Publication No. 122969. The preferred matrix in this recovery process is D-Alanyl-D-Alanine coupled with a controlled pore cross-linked polydextrane which is also described therein.

The reaction medium can be subjected to the affinity chromatography directly after filtration or after a preliminary purification procedure. This latter procedure includes making the whole medium basic, preferably between pH 8.5 and 10.5 and then filtering in the presence of a filter aid, if convenient. If the reaction medium is kept for a certain time at basic pH de-acyl antibiotic A 40926 P is transformed into de-acyl antibiotic A 40926 analogously to the transformation, under the same conditions, of the respective starting materials. (This transformation can be monitored by HPLC as usual).

The clear filtrate is then adjusted to a pH value between 7 and 8 and then subjected to an affinity chromatography on immobilized D-Alanyl-D-Alanine, either in column or batchwise.

While the binding of the substance to the affinity matrix is preferably made at a pH of about 7.0–8.0, its elution is performed at more basic pH values (preferably between 9.0 and 10.5) by means of an aqueous base. This aqueous base may be ammonia, a volatile amine, an alkali or alkali metal hydroxide or a basic buffered solution optionally in the presence of a polar organic solvent such as a polar water-miscible solvent.

Representative examples of polar water-miscible solvents are: water-soluble alcohols, (such as methanol, ethanol, iso-propanol, n-butanol), acetone, acetonitrile, lower alkyl alkanoates (such as ethyl acetate), tetrahydrofuran, dioxane and dimethylformamide and mixtures thereof; the preferred polar water-miscible solvent being acetonitrile.

After removing the impurities by rinsing the column with aqueous buffer pH 4–9, optionally containing salts, urea and/or water-miscible solvents, the de-acyl A 40926 antibiotic substance is eluted with the above eluting mixture.

This eluate is adjusted to pH 2.5–4.0 with an organic or mineral acid to remove the materials which are insoluble at this pH.

The precipitate is removed by filtration or centrifugation and the surnatant containing de-acyl A 40926 antibiotic is then conveniently desalted.

A convenient desalting procedure includes applying the antibiotic containing aqueous solution to a silanized silica gel column, washing with distilled water and eluting with a mixture of a polar water-miscible solvent as defined above and water.

Alternatively, desalting may be carried out by applying the antibiotic containing solution to the above described affinity column, washing with distilled water and eluting with a volatile aqueous base as described above for the elution of the affinity chromatography.

The obtained product, namely de-acyl A 40926 antibiotic, antibiotic A 40926 aminoglucuronyl aglycon or de-acyl antibiotic A 40926 P, is obtained substantially pure by concentrating the eluted fractions containing it (HPLC analysis) followed by precipitation by addition of a non-solvent or lyophilization.

Examples of non-solvents are water miscible ketones such as acetone or methylethyl ketone, or water-miscible alcohols such as methanol, ethanol, propanol and the like, as well as their mixtures with water-miscible organic solvents such as petroleum ether, lower alkyl ethers, such as ethyl ether, propyl-ether and butyl ether.

De-acyl antibiotic A 40926, de-acyl antibiotic A 40926 P and antibiotic A 40926 aminoglucuronyl aglycon are active against gram-positive bacteria which are responsible for many widely diffused infections. Because of the increasing resistance of these pathogens to the usual therapeutic treatments, the need for new antibiotic substances is still great.

In general, for antibacterial treatment de-acyl antibiotic A 40926, de-acyl antibiotic A 40926 P and antibiotic A 40926 aminoglucuronyl aglycon as well as the non-toxic pharmaceutically acceptable salts thereof or mixture thereof, can be administered by different routes such as, topically or parenterally. The parenteral administration is, in general, the preferred route of administration.

Compositions for injection may take such forms as suspensions, solutions, or emulsions in oily or aqueous vehicles, and may contain adjuvants such as suspending, stabilizing and/or dispersing agents.

Alternatively, the active ingredient may be in powder form for reconstitution at the time of delivery when a suitable vehicle, such as sterile water, is added thereto.

Depending on the route of administration, these compounds can be formulated into various dosage forms.

In some instances, it may be possible to formulate the compounds of the invention in enteric-coated dosage forms for oral administration which may be prepared as known in the art (see for instance "Remington's Pharmaceutical Sciences", fifteenth edition, Mack Publishing Company, Easton, Pa., U.S.A., page 1614).

This could be specially the case when the absorption of the antimicrobial substance in the enteric tract is particularly desired while passing unaltered through the gastric tract.

The amount of active principle to be administered depends on various factors such as the size and condition of the subject to be treated, the route and frequency of administration, and the causative agent involved.

The antibiotic substances of the present invention, namely de-acyl antibiotic A 40926, de-acyl antibiotic A 40926 P and antibiotic A 40926 aminoglucuronyl aglycon and the physiologically acceptable salts thereof, are generally effective at a daily dosage of between about 0.5 and 50 mg of active ingredient per kilogram of patient body weight, optionally divided into 1 to 4 administrations per day.

Particularly desirable compositions are those prepared in dosage units containing from about 100 to about 5,000 mg per unit.

Sustained-action formulations can be prepared based on different mechanisms and methods, as known in the art.

A preferred method for preparing a sustained-action formulation containing de-acyl antibiotic A 40926, de-acyl antibiotic A 40926 P or antibiotic A 40926 aminoglucuronyl aglycon, involves the use of a water insoluble form of the antibiotic suspended in an aqueous or oily medium.

Preferably, the pharmaceutical preparations of the invention, are intended for therapy (including prevention, treatment, cure, etc.) in humans, even if primates and mammalians in general as well as pet animals can also be treated with the compounds and preparations of the invention.

Preparation of pharmaceutical compositions:

A unit dosage form for intramuscular injection is prepared with 5 ml of sterile suspension USP containing 8% propylene glycol and 500 mg of a physiologically acceptable base addition salt of de-acyl antibiotic A 40926

A unit dosage form for intramuscular injection is prepared with 5 ml of sterile suspension USP containing 8% propylene glycol and 500 mg of a physiologically acceptable base addition salt of antibiotic A 40926 aminoglucuronyl aglycon.

A unit dosage form for intramuscular injection is prepared with 5 ml of sterile suspension USP containing 8% propylene glycol and 250 mg of a physiologically acceptable base addition salt of antibiotic A 40926 aminoglucuronyl aglycon.

A unit dosage form for intramuscular injection is prepared with 1,000 mg of antibiotic A 40926 aminoglucuronyl aglycon in the water-insoluble form suspended in 5 ml of sterile water for injection.

Furthermore, the antibiotic substances of the invention can be useful for suppressing the growth of *Clostridium difficile* which causes pseudomembranous colitis in the intestine. These antibiotics could be used in the treatment of pseudomembranous colitis by the oral administration of an effective dose of the antibiotics or a pharmaceutically-acceptable salt thereof, prepared in a pharmaceutically-acceptable dosage form. For such use, the antibiotics can be administered in gelatin capsules or in liquid suspension.

Besides their activity as medicaments, de-acyl antibiotic A 40926, de-acyl antibiotic A 40926 P and antibiotic A 40926 aminoglucuronyl aglycon and the pharmaceutically acceptable salts thereof, can be used as animal growth promoters.

The term "animal" in this context, is intended to encompass any non-human warm-blooded animal, in particular those bred ultimately as a source material for human consumption, and pet animals.

For this purpose, a compound of the invention is administered orally in a suitable feed. The exact concentration employed is that which is required to provide for the active agent in a growth promotant effective amount when normal amounts of feed are consumed.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed.

The way in which such feed premixes and complete rations can be prepared and administered are described in reference books (such as "Applied Animal Nutrition", W. H. Freedman and CO., S. Francisco, U.S.A., 1969 or "Livestock Feeds and Feeding" O and B books, Corvallis, Oreg., U.S.A., 1977) and are incorporated herein by reference.

The preparation of antibiotic A 40926 complex and the single factors thereof from Actinomadura sp. ATCC 39727 or a producing mutant or variant thereof is described in EP-A-177882.

Preparation of antibiotic A 40926 N-acylaminoglucuronyl aglycons:

Antibiotic A 40926 N-acylaminoglucuronyl aglycon complex AB, N-acylaminoglucuronyl aglycon factor A, N-acylaminoglucuronyl aglycon factor B, antibiotic A 40926 N-acylaminoglucuronyl aglycon factor $B_0$, antibiotic A 40926 N-acylaminoglucuronyl aglycon factor $B_1$ and antibiotic A 40926 aglycon are prepared from antibiotic A 40926 complex or a single factor or mixture of said factors in any proportion, i.e. A 40926 factor A, A 40926 factor B, A 40926 factor PA, A 40926 factor PB, A 40926 factor $B_0$ and A 40926 factor B1, by controlled acid hydrolysis.

Generally, this hydrolysis is conducted in the presence of a strong acid in a suitable organic solvent. The reaction temperature may vary considerably; preferably it is between 4° C. and 100° C. and most preferably between 25° C. and 80° C.

The reaction time varies depending on the specific reaction conditions.

Generally, the reaction time is between 30 min and 120 h. However, since the reaction course may be monitored by TLC or HPLC, the skilled man is capable of deciding when the hydrolysis of the starting materials is to be considered as completed and the recovery procedure may be started.

Representative examples of strong acids are mineral or organic strong acids such as hydrogen halides, e.g. hydrogen chloride, bromide and iodide, phosphoric acids, sulfuric acid, haloacetic acids, e.g. trichloroacetic acid, trifluoroacetic acid, chlorodifluoroacetic acid and the like.

Suitable organic solvents are such that:
a) they may at least partially solubilize the starting materials;
b) the products, once obtained, either separate or may be separated from them according to usual techniques, and
c) in any case, they do not unfavorably interfere with the reaction course.

Examples of said organic solvents are protic or aprotic solvents such as $(C_1-C_4)$alkyl sulfoxides, e.g. dimethylsulfoxide and diethylsulfoxide, $(C_1-C_4)$alkyl formamides, e.g. dimethylformamide, diethylformamide, dioxane, tetrahydrofuran and similar solvents, which are of course compatible with the selected acid.

In general, the hydrolysis is conducted in the presence of a limited amount of water, e.g. from 0.1 to 10% (w/w) of the reaction mixture. This amount of water can obviously be already present either in the starting materials, solvents and/or reagents, or may be added ad hoc, if necessary.

A preferred embodiment of this process is represented by the use of a mixture dimethylsulfoxide/concentrated hydrochloric acid at a temperature between 40° C. and 80° C. Typically, the ratio of the mixture dimethylsulfoxide/concentrated hydrochloric acid is from 8:2 to 9.5:0.5. Preferred concentrated hydrochloric acid is 37% (w/w) hydrochloric acid.

Generally, the reaction product is a mixture of the N-acyiaminoglucuronyl aglycons and the aglycon. By controlling the temperature, and in some instances also the concentration and strength of the acid, it is possible to direct the process, at least to a certain extent, to the production of one of the two main products, i.e. antibiotic A 40926 N-acylaminoglucuronyl aglycons or antibiotic A 40926 aglycon. More particularly, by keeping a comparatively low temperature, possibly reducing the strength of the acid mixture and properly controlling the reaction time, the yields in the N-acylaminoglucuronyl aglycons are increased, while at comparatively higher temperatures and longer times the aglycon alone is obtained.

Also in this case, the reaction course is monitored by TLC or preferably HPLC and the reaction may be stopped when the optimal production of the desired substance is obtained in order to maximize the yields of the subsequent recovery process.

When a product is obtained which is a mixture of antibiotic A 40926 N-acylaminoglucuronyl aglycons and antibiotic A 40926 aglycon it can be separated by chromatography such as liquid/liquid chromatography, flash chromatography, high pressure liquid chromatography and affinity chromatography.

When affinity chromatography is used, a preferred adsorbent is an immobilized D-Alanyl-D-Alanine as described in EP-A- 122969. Particularly preferred is agarose-epsilon-aminocaproyl-D-Alanyl-D-Alanine. The elution mixture is a mixture of an aqueous buffer and a saline solution. By adjusting the pH and the salt concentration antibiotic A 40926 N-acylaminoglucuronyl aglycons are separated from antibiotic A 40926 aglycon.

A preferred procedure for prevalently preparing antibiotic A 40926 N-acylaminoglucuronyl aglycon complex AB or a factor thereof is a process which comprises subjecting antibiotic A 40926 complex or a single factor thereof, antibiotic A 40926 complex AB, antibiotic A 40926 factor A, antibiotic A 40926 factor B, antibiotic A 40926 factor $B_0$, antibiotic A 40926 factor $B_1$, antibiotic A 40926 factor PA and antibiotic A 40926 factor PB to controlled acid hydrolysis with a mixture of a polar aprotic solvent and a strong mineral or organic acid in the presence of a limited (0.1–10%, w/w) amount of water at a temperature between room temperature and 100° C. and preferably between 40° C. and 65° C. for a time of from 3 h to 120 h.

Most preferably the hydrolyzing mixture is a mixture of dimethylsulfoxide and 37% hydrochloric acid from 9:1 to 9.5:0.5, the temperature is 65° C. and the reaction time is 5 h.

When the starting material for the preparation of the N-acylaminoglucuronyl aglycon is antibiotic A 40926 complex, a final product is obtained which is still a mixture of factors substantially corresponding to those of the original complex, while when a single factor is used, such as antibiotic A 40926 factor A or factor B, a single N-acylaminoglucuronyl aglycon factor is obtained which is respectively antibiotic A 40926 N-acylaminoglucuronyl aglycon factor A and antibiotic A 40926 N-acylaminoglucuronyl aglycon factor B (which can in turn be separated into factor $B_0$ and $B_1$).

When an antibiotic A 40926 N-acylaminoglucuronyl aglycon complex AB is obtained, it can be separated into its single factors by known per se techniques such as liquid/liquid chromatography and preferably preparative HPLC.

A preferred procedure includes reverse-phase liquid chromatography, preferably in stainless steel columns under moderate pressure (5–50 bar) or at high pressure (100–200 bar). The solid phase may be a silanized silica gel with a hydrocarbon phase at (2–18) carbon atoms (most preferably C 18) or phenyl group and the eluent is a mixture of a polar water-miscible solvent as defined above and an aqueous buffer at a pH compatible with the resin (preferably pH 4–8).

Most preferred is a linear gradient elution mixture of a polar water soluble aprotic solvent selected from acetonitrile and an aqueous buffer solution at pH between 4 and 8 and preferably about 6, such as a linear gradient from 5% to 45% of a mixture acetonitrile/phosphate buffer, pH 6, 70:30 and a mixture acetonitrile/phosphate buffer, pH 6, 10:90.

Antibiotic A 40926 N-acylaminoglucuronyl aglycon complex AB (in the non-addition salt form) has the following characteristics:

A) ultraviolet absorption spectrum which exhibits the following absorption maxima:

|  | $\lambda$ max (nm) |
|---|---|
| a) 0.1N HCl | 282 |
| b) phosphate buffer pH 7.4 | 282 |
|  | 310 (shoulder) |
| c) 0.1N KOH | 302 |

B) infrared absorption spectrum which exhibits the following absorption maxima ($cm^{-1}$): 3700–3100; 3000–2800 (nujol); 1650; 1620–1550; 1500; 1460 (nujol); 1375 (nujol); 1300; 1250–1180; 1150; 1060; 1010; 970; 930; 840, 820

C) $^1$H-NMR spectrum which exhibits the following groups of signals (in ppm) at 270 MHz recorded in DMSO $d_6$ (hexadeuterodimethylsulfoxide) plus $CF_3COOH$ using TMS as the internal standard (0.00 ppm), ($\delta$=ppm): 0.84, d and t [isopropylic $CH_3$'s and terminal $CH_3$]; 1.14, m [$(CH_2)_n$]; 1.44, m [—$CH_2$—C—CO and isopropylic CH]; 2.00, t [—$CH_2$—(CO)]; 2.5 s (DMSOd$_5$); 2.5 s (N—$CH_3$); 2.93, m [CH, (Z2)]; 3.33, m [CH, (Z'2)]; 3.20–3.80, m [sugar CH's]; 5.34, d [anomeric proton of acylaminoglucuronic acid]; 4.10 m (X6); 4.33 d, (X5); 4.43 d (X7); 4.9 m (X2); 5.1 (4f and Z6); 5.4 s (X1); 5.58 d (X4); 5.7 s (4b); 6.06 d (X3); 7.73 s (6b); 6.26–8.42 s and m [aromatic CH's and peptidic NH's]; 8.70–10.5, br s [phenolic OH's and $NH_2^+$]
br=broad
d=doublet
m=multiplet
s=singlet
t=triplet D) Retention times ($R_t$) of 1.20 and 1.30 relative to Teicoplanin $A_2$ component 2 ($R_t$=20.3 min) when analyzed by reverse phase HPLC under the following conditions:

column: ULTRASPHERE ODS ( 5 μm) ALTEX (Beckman) 4.6 mm (i.d.)×250 mm pre-column: Brownlee Labs RP 18 (5 μm)

| eluent A: $CH_3CN$ | 10% | adjusted at |
|---|---|---|
| (2.5 g/l) $NaH_2PO_4.H_2O$ | 90% | pH 6.0 |
| eluent B: $CH_3CN$ | 70% | adjusted at |
| (2.5 g/l) $NaH_2PO_4.H_2O$ | 30% | pH 6.0 | elution: linear gradient from 5% to 60% of eluent B in eluent A, in 40 min flow rate: 1.8 ml/min U.V. detector: 254 nm internal standard: Teicoplanin $A_2$ component 2 (Gruppo Lepetit S.p.A.)

E) acid functions capable of forming salts

F) amino function capable of forming salts

G) no mannose unit linked to the core moiety.

Antibiotic A 40926 N-acylaminoglucuronyl aglycon factor A (in the non-addition salt form) has the following characteristics:

A) ultraviolet absorption spectrum which exhibits the following absorption maxima:

| | λ max (nm) |
|---|---|
| a) 0.1N HCl | 282 |
| b) phosphate buffer pH 7.4 | 282 |
| | 310 (shoulder) |
| c) 0.1N KOH | 302 |

B) infrared absorption spectrum which exhibits the following absorption maxima ($cm^{-1}$): 3700–3000; 3000–2800; 1650; 1585; 1505; 1460 (nujol); 1375 (nujol); 1295; 1230; 1210; 1150; 1070; 1060; 1010; 845; 820; 720 (nujol)

C) 1H-NMR spectrum which exhibits the following groups of signals (in ppm) at 270 MHz recorded in DMSO $d_6$ (hexadeuterodimethylsulfoxide) using TMS as the internal standard (0.00 ppm), (δ=ppm): 0.85 t (terminal $CH_3$); 1.0–1.3 (aliphatic $CH_2$'s); 1.42 m ((OC—C)$CH_2$); 2.00 t ((CO)$CH_2$); 2.35 s ($NCH_3$); 2.49 s ($DMSOd_5$); 2.82 m (Z2); 2.8–3.8 (sugar protons and Z'2); 4.12 m (X6); 4.56 s (X1); 4.34 d (X5); 4.41 d (X7); 4.96 m (X2); 5.08–5.12 (4f and Z6); 5.40 d (anomeric proton of acylaminoglucuronic acid); 5.58 d (X4); 5.74 s (4b); 6.05 d (X3); 7.75 s (6b); 6.25–8.40 s, d and m (aromatic CH's and peptidic NH's)

D) Retention time ($R_t$) of 1.20 relative to Teicoplanin $A_2$ component 2 ($R_t$=20.3 min) when analyzed by reverse phase HPLC under the following conditions:

column: ULTRASPHERE ODS (5 μM) ALTEX (Beckman)
4.6 mm (i.d.)×250 nun pre-column: Brownlee Labs RP 18 (5 μm)

| eluent A: $CH_3CN$ | 10% | } adjusted at |
| --- | --- | --- |
| (2.5 g/l) $NaH_2PO_4 \cdot H_2O$ | 90% | } pH 6.0 |
| eluent B: $CH_3CN$ | 70% | } adjusted at |
| (2.5 g/l) $NaH_2PO_4 \cdot H_2O$ | 30% | } pH 6.0 | elution: linear gradient from 5% to 60% of eluent B in eluent A, in 40 min flow rate: 1.8 ml/min U.V. detector: 254 nm internal standard: Teicoplanin $A_2$ component 2 (Gruppo Lepetit S.p.A.)

E) Molecular weight of about 1554 as determined by FAB-MS

F) acid functions capable of forming salts

G) amino function capable of forming salts

H) no mannose unit linked to the core moiety.

Antibiotic A 40926 N-acylaminoglucuronyl aglycon factor $B_0$ (in the non-addition salt form) has the following characteristics:

A) ultraviolet absorption spectrum which exhibits the following absorption maxima:

| | λ max (nm) |
|---|---|
| a) 0.1N HCl | 282 |
| b) phosphate buffer pH 7.4 | 282 |
| | 310 (shoulder) |
| c) 0.1N KOH | 302 |

B) infrared absorption spectrum which exhibits the following absorption maxima ($cm^{-1}$): 3700–3100; 3000–2800 (nujol); 1650; 1585; 1505; 1460 (nujol); 1375 (nujol); 1295; 1230; 1210; 1150; 1060; 1010; 980; 840; 820; 720 (nujol)

C) $^1$H-NMR spectrum which exhibits the following groups of signals (in ppm) at 270 MHz recorded in DMSO $d_6$ (hexadeuterodimethylsulfoxide) using TMS as the internal standard (0.00 ppm), (δ=ppm): 0.84, d (isopropylic $CH_3$'s); 1.0–1.3 (aliphatic $CH_2$'s); 1.3–1.6 ((OC—C)—$CH_2$ and isopropylic —CH); 2.00 t ((OC)$CH_2$); 2.32 s ($NCH_3$); 2.49 s ($DMSOd_5$); 2.82 m (Z 2); 2.9–3.8 (sugar protons); 4.12 m (X6); 4.44 s (X1); 4.33 d (X5); 4.37 d (X7); 4.95 m (X2); 5.06–5.10 (4f and Z6); 5.38 d (anomeric proton of acylaminoglucuronic acid); 5.59 d (X4); 5.72 s (4b); 6.05 d (X3); 7.74 s (6b); 6.27–8.5 (aromatic and peptidic NH's)

D) Retention time ($R_t$) of 1.30 relative to Teicoplanin $A_2$ component 2 ($R_t$=20.3 min) when analyzed by reverse phase HPLC under the following conditions:

column: ULTRASPHERE ODS (5 μm) ALTEX (Beckman) 4.6 mm (i.d.)×250 mm.

pre-column: Brownlee Labs RP 18 (5 μm)

| eluent A: $CH_3CN$ | 10% | } adjusted at |
| --- | --- | --- |
| (2.5 g/l) $NaH_2PO_4 \cdot H_2O$ | 90% | } pH 6.0 |
| eluent B: $CH_3CN$ | 70% | } adjusted at |
| (2.5 g/l) $NaH_2PO_4 \cdot H_2O$ | 30% | } pH 6.0 | elution: linear gradient from 5% to 60% of eluent B in eluent A, in 40 min flow rate: 1.8 ml/min U.V. detector: 254 nm internal standard: Teicoplanin $A_2$ component 2 (Gruppo Lepetit S.p.A. )

E) Molecular weight of about 1568 as determined by FAB-MS

F) acid functions capable of forming salts

G) amino function capable of forming salts

H) no mannose unit linked to the core moiety.

Antibiotic A 40926 N-acylaminoglucuronyl aglycon factor $B_1$ (in the non-addition salt form) has the following characteristics:

has molecular weight of about 1568 as determined by FAB-MS and substantially the same physico-chemical characteristics reported above for antibiotic A 40926 N-acylaminoglucuronyl aglycon factor $B_0$ except that it has a triplet at 0.84 δ ppm attributable to the methyl group of an n-propyl function in the NMR system reported above and a retention time relative to Teicoplanin $A_2$ component 2 of 1.32 in the system reported above.

The following "preparations" are an example of the way in which antibiotic A 40926 N-acylaminoglucuronyl aglycon complex and the factors thereof can be prepared:

Preparation 1:

Preparation of antibiotic A 40926 N-acylaminoglucuronyl aglycon complex AB a) Antibiotic A 40926 complex AB (prepared substantially by following the procedure of Example 3 of EP-A-177882) (750 mg) is dissolved in 150 ml of a mixture dimethylsulfoxide (DMSO)/37% (w/w) hydrochloric acid (HCl), 9:1 (v/v) and the reaction mixture is heated to about 65° C. The reaction course is monitored by HPLC and when the starting materials are completely reacted (after about 5 h) the reaction is quenched with cold water (600 ml) and the pH of the resulting mixture is adjusted to about 7.5. This mixture contains a mixture of the compounds of the title which is separated into its two major components by affinity chromatography according to the following procedure:

b) The aqueous mixture obtained above (750 ml) is applied to a SEPHAROSE-D-Alanyl-D-Alanine chromatography column prepared as described in EP-A-177882 and EP-A-122969, Example 1.A) (100 ml of swollen resin in 10 mM TRIS.HCl pH 7.5 buffer; bed height 10 cm). 0.05M $NH_4OH.HCl$ pH 7.5 containing 2M NaCl (200 ml) (buffer B) is passed through the column; then A 40926 aglycon is selectively removed from the column by eluting with 0.05M $NH_4OH.HCl$ pH 9.5 containing 2M NaCl (1500 ml) (buffer C). N-Acylaminoglucuronyl aglycon complex AB is then eluted with 0.1M aqueous ammonia (buffer D). The eluted fractions are then pooled according to their antibiotic content adjusted to about pH 7.5 and each antibiotic containing solution is chromatographed on a SEPHAROSE-D-Alanyl-D-Alanine column (100 ml of swollen resin in 10 mM TRIS.HCl pH 7.5 buffer; bed height 10 cm). Distilled water is passed through the column until the inorganic salts are washed out. The antibiotics are then eluted with 0.1N aqueous ammonia. These eluted fractions, pooled according to their antibiotic content, are concentrated to a small volume under reduced pressure by azeotropical distillation with n-butanol and lyophilized yielding respectively 201 mg of N-acylaminoglucuronyl aglycon complex AB and 236 mg of A 40926 aglycon.

By repeating the same experiment described above but using a mixture DMSO/37% HCl 95:5 at about 40° C. for about 5 days the yield in N-acylaminoglucuronyl aglycon complex AB increases of about 15% while the yield in A 40926 aglycon is reduced accordingly.

By repeating these experiments starting from antibiotic A 40926 complex, antibiotic A 40926 factor A, antibiotic A 40926 factor B, antibiotic A 40926 factor $B_0$, antibiotic A 40926 factor $B_1$, antibiotic A 40926 factor PA and antibiotic A 40926 factor PB substantially the same results are obtained (i.e. the yields vary in the range ±5%). In particular, starting from antibiotic A 40926 factor A, or factor PA, the product which is obtained is antibiotic A 40926 N-acylaminoglucuronyl aglycon factor A, starting from antibiotic A 40926 factor $PB_0$, or factor $B_0$ the obtained product is antibiotic A 40926 N-acylaminoglucuronyl aglycon factor $B_0$, starting from antibiotic A 40926 factor B or PB the obtained product is antibiotic A 40926 N-acylaminoglucuronyl aglycon factor B, which may in turn be separated into factor $B_0$ and $B_1$, and starting from antibiotic A 40926 factor $B_1$, antibiotic A 40926 N-acylaminoglucuronyl aglycon factor $B_1$ is obtained.

Preparation 2:

Separation of antibiotic A 40926 N-acylaminoglucuronyl aglycon factors A, B0 and $B_1$ 20 Mg of antibiotic A 40926 N-acylaminoglucuronyl aglycon complex AB is dissolved in 1 ml of 18 mM sodium phosphate buffer pH 6.0 containing 10% of acetonitrile. The solution was injected into a HPLC preparative column (7 mm id×250 mm) LICHROSORB RP18 silanized silica gel (Merck Co.) having 7 micrometer particle size. The column is eluted at a flow rate of 5 ml/min of phase A and B with a linear gradient from 10% to 55% of phase A in 55 min.

Phase A: 18 mM sodium phosphate/$CH_3CN$ 30/70 brought to pH 6.0 with NaOH.

Phase B: 18 mM sodium phosphate/$CH_3CN$ $_{90/10}$ brought to pH 6.0 with NaOH.

The column eluates UV adsorption at 254 nm is recorded and the elution fractions having omogeneous content are collected, separating three groups of eluates containing antibiotic A 40926 N-acylaminoglucuronyl aglycon factors A, $B_0$ and $B_1$ respectively.

The eluates containing the purified antibiotic A 40926 N-acylaminoglucuronyl aglycon factors of 11 subsequent chromatographic runs are pooled and desalted as usual by loading them on a column of 5 ml swollen SEPHAROSE-D-Ala-D-Ala (see above). After removing the salts with 10 ml of 1 mM HCl followed by 5×10 ml of distilled water, the antibiotic is eluted with 5×10 ml of 1% w/v aqueous ammonia. The ammonia eluates are then separately collected and freeze-dried yielding 15 mg of antibiotic A 40926 N-acylaminoglucuronyl aglycon factor A, 51 mg of antibiotic A 40926 N-acylaminoglucuronyl aglycon factor $B_0$ and 3 mg of antibiotic A 40926 N-acylaminoglucuronyl aglycon factor $B_1$ whose physico-chemical data and chemical formula are reported above in the description.

The following examples further illustrate the invention and, as such, should not be construed as limiting its scope.

EXAMPLE 1

Fermentation of *Actinoplanes teichomyceticus*

A sample of a frozen stock culture of *Actinoplanes teichomyceticus* ATCC 31121 is used to inoculate 100 ml of vegetative medium having the following composition:

| | |
|---|---|
| Glucose | 10 g |
| Peptone | 4 g |
| Yeast extract | 4 g |
| $MgSO_4$ | 0.5 g |
| $KH_2PO_4$ | 2 g |
| $K_2HPO_4$ | 4 g |
| Deionized water | 1000 ml |

100 ml of the inoculated medium is incubated 48 hours in a 500 ml Erlenmeyer flask at 28° C. on a rotary shaker. 200 ml of this culture is used to inoculate 4 l of fermentation medium having the following composition:

| | |
|---|---|
| Peptone | 4 g |
| Yeast extract | 1 g |
| Soybean meal | 10 g |
| Malt extract | 4 g |
| Glucose | 5 g |
| NaCl | 2.5 g |
| $CaCO_3$ | 5 g |
| Deionized water | 1000 ml |

The inoculated medium is fermented at about 28° C. under 0.5 v/v/min steril air flow at about 900 rpm for about 48 h. *Actinoplanes teichomyceticus* ATCC 53649 can be used instead of *Actinoplanes teichomyceticus* ATCC 31121.

EXAMPLE 2

Fermentation of *Actinoplanes missouriensis* ATCC 23342

A lyophilized tube containing *Actinoplanes missouriensis* strain ATCC 23342 is open and aseptically transferred into a slant of oatmeal agar. After a 12 day incubation at 28° C., the culture is suspended in distilled water and inoculated into 10 Erlenmeyer-flasks each containing 100 ml of medium having the following composition:

| | |
|---|---|
| Yeast extract | 2 g |
| Soybean meal | 8 g |
| Dextrose | 20 g |
| NaCl | 1 g |
| $CaCO_3$ | 4 g |
| $H_2O$ | 1000 ml |

The inoculated medium is incubated 48 hours at 30° C. on a rotary shaker at 200 rpm.

*Actinoplanes missouriensis* NRRL 15646, NRRL 15647, ATCC 31683, ATCC 31682, ATCC 32680 or a mixture thereof in any proportion, can be used instead of Actinoplanes missouriensis ATCC 23342.

EXAMPLE 3:

Fermentation of Actinoplanes NRRL 3884

A lyophilized tube containing Actinoplanes strain NRRL 3884 is open and aseptically transferred into a slant of oatmeal agar. After a 12 day incubation at 28° C., the culture is suspended in distilled water and inoculated into 10 Erlenmeyer flasks each containing 100 ml of medium having the following composition:

| | |
|---|---|
| Yeast extract | 2 g |
| Soybean meal | 8 g |
| Dextrose | 20 g |
| NaCl | 1 g |
| $CaCO_3$ | 4 g |
| $H_2O$ | 1000 ml |

The inoculated medium is incubated 48 hours at 30° C. on a rotary shaker at 200 rpm.

EXAMPLE 4

Preparation of de-acyl antibiotic A 40926 a) Biotransformation of antibiotic A 40926 complex AB

Antibiotic A 40926 complex AB (prepared substantially as described in EP-A-177882) is aseptically added to the fermenting culture prepared substantially as described in Example 1, 2 or 3, 48 hours after inoculum. The biotransformation process is monitored by HPLC analysis of the broth. Glycopeptide antibiotics are purified on SEPHAROSE-D-Alanyl-D-alanine (see EP-A-122969) and are analyzed according to the following HPLC method:

Column: ultraSphere ODS (5 μm) 4.6 mm×25 cm. ALTEX (Beckman)

Precolumn: Brownlee labs RP18 (5 μm)

Phase A: 18 mM sodium phosphate buffer/$CH_3CN$ 98/2 (v/v) brought to pH 6.0 with NaOH Phase B: 18 mM sodium phosphate buffer/$CH_3CN$ 30/70 (v/v) brought to pH 6.0 with NaOH Elution: linear gradient from 5% to 65% of phase B in 43 min Flow rate: 1.8 ml/min Detection: UV 254 nm The retention time of de-acyl antibiotic A 40926 is in the range 8.3 and 9.

The harvesting time is set at about 196 hours after the addition of antibiotic A 40926 complex AB to the medium for Actinoplanes NRRL 3884, about 168 hours for *Actinoplanes missouriensis* ATCC 23342, ATCC 31683, ATCC 31682, ATCC 32680, NRRL 15646 and NRRL 15647 and about 192 hours for *Actinoplanes teichomyceticus* ATCC 31121 and ATCC 53649. The deacylation efficiency is substantially similar with any of the above cultures.

b) Recovery and purification

The harvested broth obtained from the pooled Erlenmeyer flasks is brought to pH 9.5 with NaOH and filtered with HYFLO-FLOMA filter aid. The filter cake is discharged while the clear filtrate is adjusted to pH 7.5 with HCl 1.10 M1 of swollen SEPHAROSE-D-Alanyl-D-Alanine (see above) is added and this mixture is stirred overnight at room temperature. The resin is then recovered by filtration and washed sequentially on the filter with 4×40 ml of 40 m MTRIS.HCl buffer (pH 6.5) [2-amino-2-hydroxy-methyl-1, 3-propanediol] and 6×40 ml of distilled water. Then, a mixture is eluted from the resin with 3×40 ml of 1% (w/v) aqueous $NH_4OH$. This solution is cooled to about 4° C. and brought to about pH 3.5 with $H_2SO_4$. The precipitate is removed by centrifugation, while the surnatant that contains the biotransformed antibiotic A 40926 in a solution (150 ml) is brought to about pH 7.0 with NaOH and loaded on a column (diameter 1 cm) containing 25 ml of SEPHAROSE-D-Alanyl-D-Alanine swollen in distilled water. The column is eluted sequentially with 50 ml of distilled water and 200 ml of ethanol/water 1/9 (v/v). The antibiotic substance of the title is then eluted with 35 ml of 1% (.w/v) aqueous $NH_4OH$. This solution is concentrated under vacuum and then freeze-dried yielding 41–45 mg of de-acyl antibiotic A 40926. The physico-chemical characteristics are reported above in the description.

By repeating the same procedure starting from antibiotic A 40926 factor A or antibiotic A 40926 factor B or $B_0$ the same compound is obtained with similar yields.

EXAMPLE 5

Preparation of antibiotic A 40926 aminoglucuronyl aglycon

If the procedure of example 4 is repeated starting from antibiotic A 40926 N-acylaminoglucuronyl aglycon complex AB, antibiotic A 40926 N-acylaminoglucuronyl aglycon factor A, factor B, factor $B_0$ or $B_1$ (prepared as described above) antibiotic A 40926 aminoglucuronyl aglycon is obtained which has the characteristics reported above in the description.

EXAMPLE 6

Preparation of de-acyl antibiotic A 40926 P

By repeating the procedure of example 4 but starting from antibiotic A 40926 factor PA or factor PB, or a mixture thereof in any proportion and reducing to a minimum the permanence of the reaction mass at basic pH values, de-acyl antibiotic A 40926 P is obtained whose characteristics are as reported above.

We claim:

1. A de-acyl A 40926 antibiotic of formula:

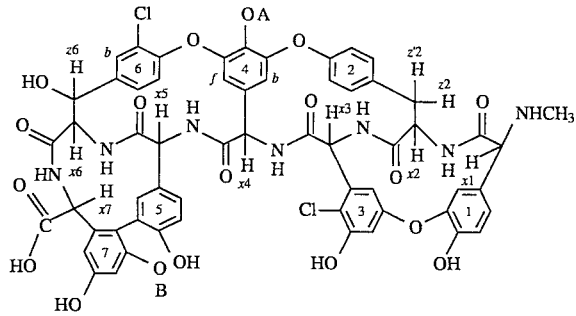

wherein:
A represents a 2-amino-2-deoxy-beta-D-glucopyranosiduronic acid group and
B represents hydrogen, alpha-D-mannopyranosyl or 6-acetyl-alpha-D-mannopyranosyl,
or the addition salt thereof.

2. De-acyl antibiotic A 40926 or an addition salt thereof, which has the following characteristics, in the non addition-salt form:

A) ultraviolet absorption spectrum which exhibits the following absorption maxima:

|  | λ max (nm) |
|---|---|
| a) 0.1M HCl | 282 |
| b) phosphate buffer pH 6.0 | 281 |
| c) phosphate buffer pH 7.4 | 282, 300 (shoulder) |
| d) 0.1M KOH | 300 |

B) infrared absorption spectrum which exhibits the following absorption maxima in nujol mull (ν, cm$^{-1}$): 3700–3100; 3000–2800 (nujol); 1650; 1590; 1505; 1460 (nujol); 1375 (nujol); 1300; 1230, 1210, 1150, 1060, 1030, 970, 810, 720 (nujol)

C) $^1$H-NMR spectrum which exhibits the following groups of signals (in ppm) at 270 MHz recorded in DMSO d$_6$ (hexadeuterodimethylsulfoxide) [(δ, ppm; m; (attributions)] 2.30, s (N—CH$_3$); 2.49, s (DMSOd$_5$); 2.7–3.8, m (sugar CH's); 2.79 m (Z2); 4.08 m (X6); 4.33 s (X1); 4.37 d (X5); 4.37 d (X7); 4.86 m (X2); 5.08 s (4f); 5.08 s (Z6); 5.27 s (anomeric proton of mannose); 5.35 d (anomeric proton of aminoglucuronic acid); 5.61 d (X4); 5.86 s (4b); 6.05, d (X3); 7.73 s (6b); 6.45–8.49 (aromatic protons and peptidic NH's)

D) Retention time (R$_t$) of 0.34 relative to Vancomycin
Column: Silanized silica gel ODS (5 μm) 4.6 mm×25 cm
Isocratic elution with 18 mM sodium phosphate buffer/CH$_3$CN 92/8 (v/v)
Flow rate: 1.8 ml/min
Detection: UV 254 nm Internal standard: Vancomycin R$_t$ 8.4 min E) molecular weight of 1548 as determined by FAB-MS spectroscopy.

3. Antibiotic A 40926 aminoglucuronyl aglycon which is a compound of claim 1 wherein A is as defined and B represents hydrogen, or an addition salt thereof.

4. De-acyl antibiotic A 40926 P which is a compound of claim 1 wherein A is as defined and B represents 6-acetyl-alpha-D-mannopyranosyl or an addition salt thereof.

5. De-acyl antibiotic A 40926 which is a compound of claim 1 wherein A is as defined and B represents alpha-D-mannopyranosyl, or an addition salt thereof.

6. A pharmaceutical composition which contains an antibacterial quantity a compound of claim 1 in admixture with a pharmaeutically acceptable carrier.

7. A method of treatment of bacterial infections of susceptible organisms comprising administering to a patient in need thereof, an antibacterial quantity of a compound of claim 1 or claim 2.

8. A method of treatment of bacterial infections of gram positive organisms comprising administering to a patient in need thereof, an antibacterial quantity of a compound of claim 1 or 2.

9. A method of treatment of bacterial infections of Neisseria comprising administering to a patient in need thereof, an antibacterial quantity of a compound of claim 1 or 2.

10. A method of treatment of bacterial infections of clostridium comprising administering to a patient in need thereof, an antibacterial quantity of a compound of claim 1 or 2.

* * * * *